United States Patent
Nakao

(10) Patent No.: US 7,512,473 B2
(45) Date of Patent: Mar. 31, 2009

(54) METHOD FOR JUDGING ROAD SURFACE CONDITION AND DEVICE THEREOF, AND PROGRAM FOR JUDGING ROAD SURFACE CONDITION

(75) Inventor: Yukio Nakao, Kobe (JP)

(73) Assignee: Sumitomo Rubber Industries, Ltd., Kobe-shi (JP)

( * ) Notice: Subject to any disclaimer, the term of this patent is extended or adjusted under 35 U.S.C. 154(b) by 409 days.

(21) Appl. No.: 10/956,055

(22) Filed: Oct. 4, 2004

(65) Prior Publication Data
US 2005/0102086 A1 May 12, 2005

(30) Foreign Application Priority Data
Nov. 6, 2003 (JP) .............................. 2003-376710

(51) Int. Cl.
*B60T 7/12* (2006.01)
*G05D 1/00* (2006.01)
(52) U.S. Cl. .............................. 701/74; 701/80; 701/90; 701/73
(58) Field of Classification Search ............... 701/80, 701/74, 90, 3; 303/165–166, 150
See application file for complete search history.

(56) References Cited

U.S. PATENT DOCUMENTS 6,650,988 B2  11/2003  Kawasaki et al.
7,389,170 B2*  6/2008  Nakao ........................ 701/80
2003/0117015 A1*  6/2003  Kuwajima et al. .......... 303/150
2003/0192375 A1*  10/2003  Sugai et al. .................. 73/146
2005/0102086 A1*  5/2005  Nakao ........................ 701/80

FOREIGN PATENT DOCUMENTS

| DE | 4300048 A1 | 10/1994 |
| EP | 1132271 A2 | 9/2001 |
| EP | 1302378 A2 | 4/2003 |
| JP | 60-99757 A | 6/1985 |
| JP | 1-249559 A | 10/1989 |
| JP | 2001-253334 A | 9/2001 |
| JP | 2002-36837 A | 2/2002 |
| JP | 2002-37046 * | 6/2002 |
| JP | 2002-274357 A | 9/2002 |
| JP | 2003-118555 A | 4/2003 |

\* cited by examiner

*Primary Examiner*—Cuong H Nguyen
(74) *Attorney, Agent, or Firm*—Birch, Stewart, Kolasch & Birch, LLP

(57) ABSTRACT

A judgment method of road surface condition includes steps of: periodically detecting the wheel rotational speeds of the four wheel tires of a vehicle, memorizing the wheel rotational speed of each of tires, determining a slip ratio from said wheel rotational speeds, determining the acceleration or deceleration of the vehicle, determining a relation equation between said slip ratio and the acceleration or deceleration of the vehicle, determining a judgment value for judging a friction coefficient between the road surface and tires based on the slope of said relation equation determined, and setting a threshold which is used for judging the friction coefficient from the judgment value using the information of wireless tags which were buried in the tires.

6 Claims, 2 Drawing Sheets

METHOD FOR JUDGING ROAD SURFACE CONDITION AND DEVICE THEREOF, AND PROGRAM FOR JUDGING ROAD SURFACE CONDITION

This Non-provisional application claims priority under 35 U.S.C. § 119(a) on Patent Application No(s). 2003-376710 filed in Japan on Nov. 6, 2003, the entire contents of which are hereby incorporated by reference.

BACKGROUND OF THE INVETNION

The present invention relates to a method for judging road surface condition and a device thereof, and a program for judging road surface condition. More specifically, the present invention relates to a judging method of road surface condition which can improve the performance and running safety of a vehicle by judging the road surface and the abrasion condition of tires, and a device thereof; and a program for judging the road surface condition.

There have been conventionally proposed an antilock brake device and the like which lower braking torque which acts on wheels before braking force between tires and road surface exceeds a maximum value and the tires become in a lock condition, prevent the lock condition of wheels, and control the rotational number of wheels by which the maximum braking force is obtained (for example, Japanese Unexamined Patent Publication No. 99757/1985 and Japanese Unexamined Patent Publication No. 249559/1989). For example, the friction coefficient of the road surface, $\mu$ is utilized in the control of the antilock brake device, and an optimum control is designed to be carried out by changing the content of control in accordance with the friction coefficient of the road surface, $\mu$ (road surface, $\mu$), for example, between a case of high $\mu$ and a case of low $\mu$.

As the friction coefficient of the road surface-judging device which judges such road surface, $\mu$, there is a device which determines a relation equation between a slip ratio and the acceleration or deceleration of a vehicle, and then judges the friction coefficient between the road surface and tires based on the slope of said relation equation (Japanese Unexamined Patent Publication No. 253334/2001). The road surface $\mu$ is designed to be judged by the threshold of a linear regression coefficient, K1 between a slip ratio and the acceleration or deceleration of a vehicle, for the slope.

However, since the threshold for judging the slipperiness of the road surface is preliminarily input from past data, it is required to input the threshold again when tires are replaced with the different kinds of tires.

Then, there are a road surface condition-judging device (Japanese Unexamined Patent Publication No. 274357/2002) in which after a correlative coefficient and the linear regression coefficient between a slip ratio and the acceleration or deceleration of a vehicle are determined, the threshold of judging the road surface condition is set based on the linear regression coefficient when said correlative coefficient is a fixed value or more, and a road surface condition-judging device (Japanese Unexamined Patent Publication No. 118555/2003) in which after the slip ratio of the front and rear wheels at left side to the front and rear wheels at right side and the slip ratio of the front and rear wheels are respectively calculated, the fluctuation quantity of difference of said left and right slip ratios is calculated, and then the threshold of judging the road surface condition is set based on the linear regression coefficient between the slip ratio of the front and rear wheels and the acceleration or deceleration of a vehicle when said fluctuation quantity is a fixed value, and the like.

Further, when tires are abraded, the thickness of tread rubbers of tires becomes thin, therefore the back and forth rigidity of a pattern becomes large. When tires are abraded, tires for winter affect performance on snow and tires for summer affect hydroplaning performance. Accordingly, it is also useful to detect the abrasion. For example, as a road surface condition-detecting device of judging that the abrasion of tires proceeds, there is a device (Japanese Unexamined Patent Publication No. 36837/2002) in which the abrasion of tires is designed to be detected by comparing the mutual linear regression coefficient between the slip ratio and the acceleration or deceleration of a vehicle with frequency distribution which is preliminarily grasped.

SUMMARY OF THE INVENTION

However, for the road surface condition-judging device, when tires were exchanged, the threshold is not immediately changed, and a vehicle must run for a long time until the threshold is changed.

Further, for the abrasion condition-detecting device, when used tires were installed, the abrasion from new articles cannot be detected, therefore when studless winter tires are installed for 2 to 3 seasons in winter, the proceeding degree of the abrasion cannot be correctly judged.

Under the circumstances, an object of the present invention is to provide a method for judging condition of road surface which can judge the road surface and can improve the performance and running safety of a vehicle by judging the abrasion condition of tires, and a device thereof; and a program for judging the road surface condition.

The judgment method of road surface condition of the present invention is characterized by comprising steps of: periodically detecting the wheel rotational speeds of the four wheel tires of a vehicle, memorizing the wheel rotational speed of each of tires, determining a slip ratio from said wheel rotational speed, determining the acceleration or deceleration of the vehicle, determining a relation equation between said slip ratio and the acceleration or deceleration of the vehicle, determining a judgment value for judging a friction coefficient between the road surface and tires based on the slope of said relation equation determined, and setting a threshold which is used for judging the friction coefficient from the judgment value using the information of wireless tags which were buried in the tires.

Further, the judgment device of road surface condition of the present invention is characterized by being equipped with a wheel speed-detecting means of periodically detecting the wheel rotational speeds of the four wheel tires of a vehicle, a memory means of memorizing the wheel rotational speed of each of tires, a slip ratio-calculating means of determining a slip ratio from said wheel rotational speed, an acceleration deceleration-calculating means of determining the acceleration or deceleration of the vehicle, a relation equation-calculating means of determining a relation equation between said slip ratio and the acceleration or deceleration of the vehicle, a judgment value-calculating means of determining a judgment value for judging a friction coefficient between the road surface and tires based on the slope of said relation equation determined, and a threshold-setting means of setting a threshold which is used for judging the friction coefficient from the judgment value using the information of wireless tags which were buried in the tires.

Furthermore, the program for judging road surface condition of the present invention is characterized by functionalizing a computer as a memory means of memorizing the wheel rotational speed of each of tires, a slip ratio-calculating means of determining a slip ratio from said wheel rotational speed, an acceleration deceleration-calculating means of determining the acceleration or deceleration of the vehicle, a relation equation-calculating means of determining a relation equation between said slip ratio and the acceleration or deceleration of the vehicle, a judgment value-calculating means of determining a judgment value for judging a friction coefficient between the road surface and tires based on the slope of said relation equation determined, and a threshold-setting means of setting a threshold which is used for judging the friction coefficient from the judgment value using the information of wireless tags which were buried in the tires, in order to judge the condition of road surface.

According to the present invention, the generation of false alarm can be prevented by changing the threshold which is the judgment basis of slipperiness of the road surface by the transmitting information of wireless tags. Referring to Examples described later, the thresholds of tires B, C and D whose threshold data are not preserved can be calculated as 0.126, 0.113 and 0.097 from the threshold of 0.098 which is memorized in tires A. The threshold of judging the slipperiness of road surface is changed in accordance with the kind of tires by the transmitting information of wireless tags, a false alarm is not emitted on an asphalt road, and an alarm is emitted at running on a porcelain tile road having low friction coefficient, therefore the road surface condition can be accurately judged.

Further, according to the present invention, the degree of abrasion can be judged by comparing the judgment threshold of the slipperiness of road surface which was changed by the transmitting information of wireless tags, with the average judgment value in tires installed. Referring to Example 2 described later, since the judgment threshold of basic tires is 0.10 and the judgment threshold of the slipperiness of studless winter tires is 0.13, the average judgment value is nearly equal against the threshold of basic tires when the average judgment value of the slipperiness is 0.11 (an abrasion of 25%) or 0.10 (an abrasion of 50%). Accordingly, since it is small against the proper threshold of 0.13, it can be judged that abrasion proceeds.

According to the present invention, the optimum control in accordance with the slipperiness of road surface can be carried out by using the information of the slipperiness of road surface which was judged as described above, to an ABS (antilock braking system) device, a TRC (traction control) device and the like. Further, when it was judged that the slipperiness is high, it can be informed that a driver should take care of slippery road surface.

For example, the ABS device can set the upper limit of brake-operating force in accordance with the slipperiness of road surface by inputting the slipperiness of road surface during running from the judgment device of road surface condition of the present invention. The ABS device detects momentarily slip (tire lock), and controls the brake-operating force in real time. The ABS device can obtain the maximum breaking force just before tire lock by setting the upper limit of the brake-operating force in accordance with road surface condition, and safer and surer brake can be realized. As a result, when a vehicle runs by installing studless winter tires on road surface on which it began to rain, road surface on which dust was washed off by rain, and road surface on which it snowed (slipperiness differs depending on temperature), brake control can be carried out in accordance with situation between tires and frozen road surface or road surface such as a pebble road.

The TRC device can realize the more effective drive control of a vehicle by inputting the slipperiness of road surface from the judgment device of road surface condition of the present invention, for example, controlling the allotment of driving force of left and right wheels, and preventing slip at take-off and acceleration by setting the upper limit of driving force in accordance with the slipperiness of road surface. For example, it can control a vehicle to an appropriate driving force even on a snow slope way and can avoid slip.

DETAILED DESCRIPTION

The judgment method of road surface condition and a device thereof, and the program for judging road surface condition of the present invention are illustrated below based on the attached drawings.

Figure 1:
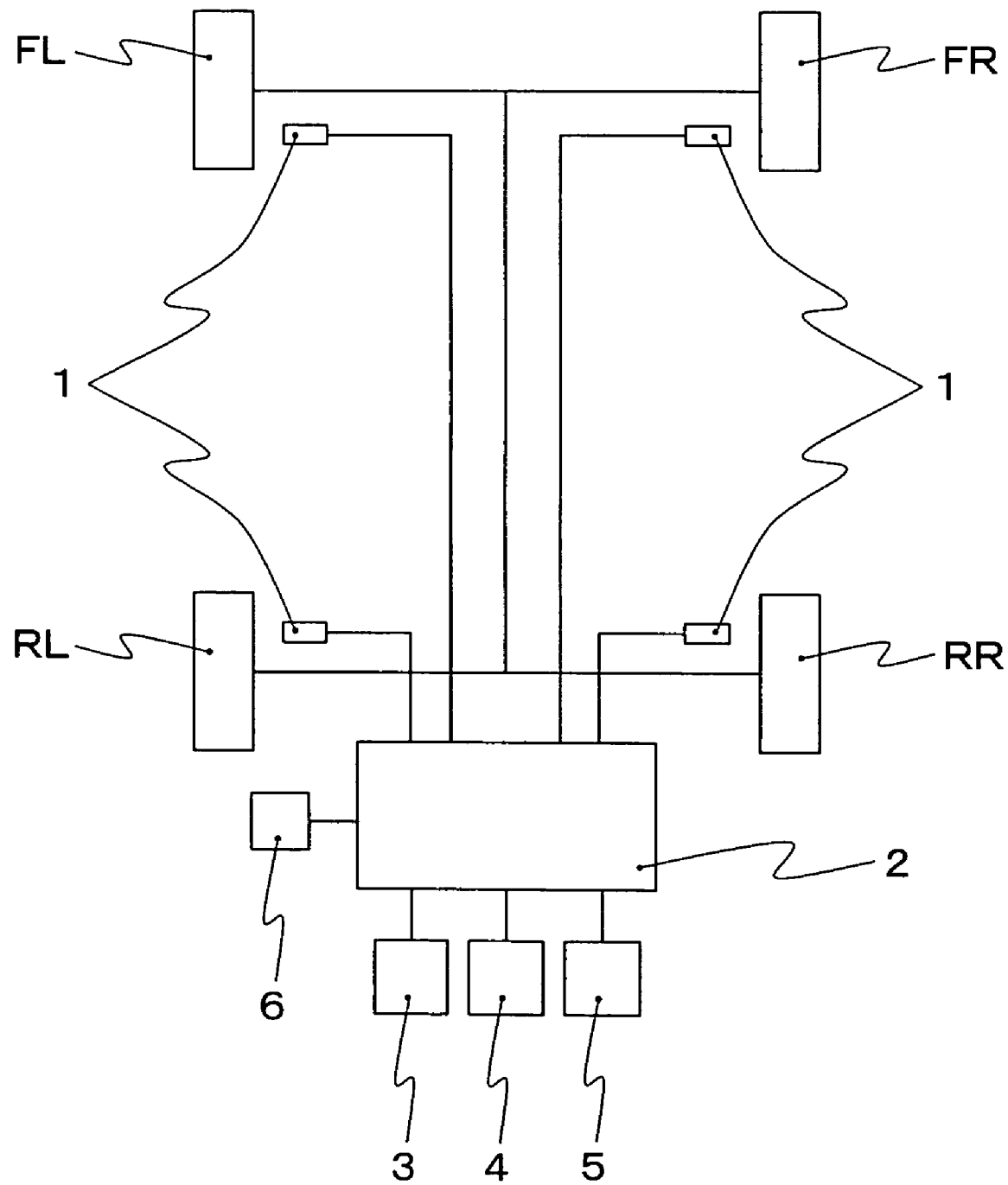
FIG. 1 is a block chart showing the road surface condition-judging device related to one embodiment of the present invention.

As represented in FIG. 1, the judgment device of road surface condition related to a embodiment of the present invention is equipped with the usual wheel speed-detecting means 1 which were provided respectively relating to four tires, FL, FR, RL and RR which were provided on a vehicle.

As the wheel speed-detecting means 1, there can be used a wheel speed sensor for generating rotational pulses using an electromagnetic pickup and the like and periodically measuring wheel rotational information such as rotational angular velocity and rotational velocity from the number of pulses, or an angular velocity sensor including those which generate power utilizing rotation such as a dynamo and measure rotational angular velocity and rotational velocity from the voltage. The output of the wheel speed-detecting means 1 is provided to the control unit 2 being a computer such as ABS. A display device 3 which is composed by a liquid crystal display for informing tires whose air pressure was lowered, a plasma display device or CRT and the like, an initialization switch 4 which can be operated by a driver, and an alarm unit 5 are connected with the control unit 2. Further, wireless tags are buried in tires. As such wireless tags, for example, V720-D52P30 (trade name, manufactured by OMRON Co.) can be used. The reader 6 of the wireless tags is connected with the control unit 2.

Figure 2:
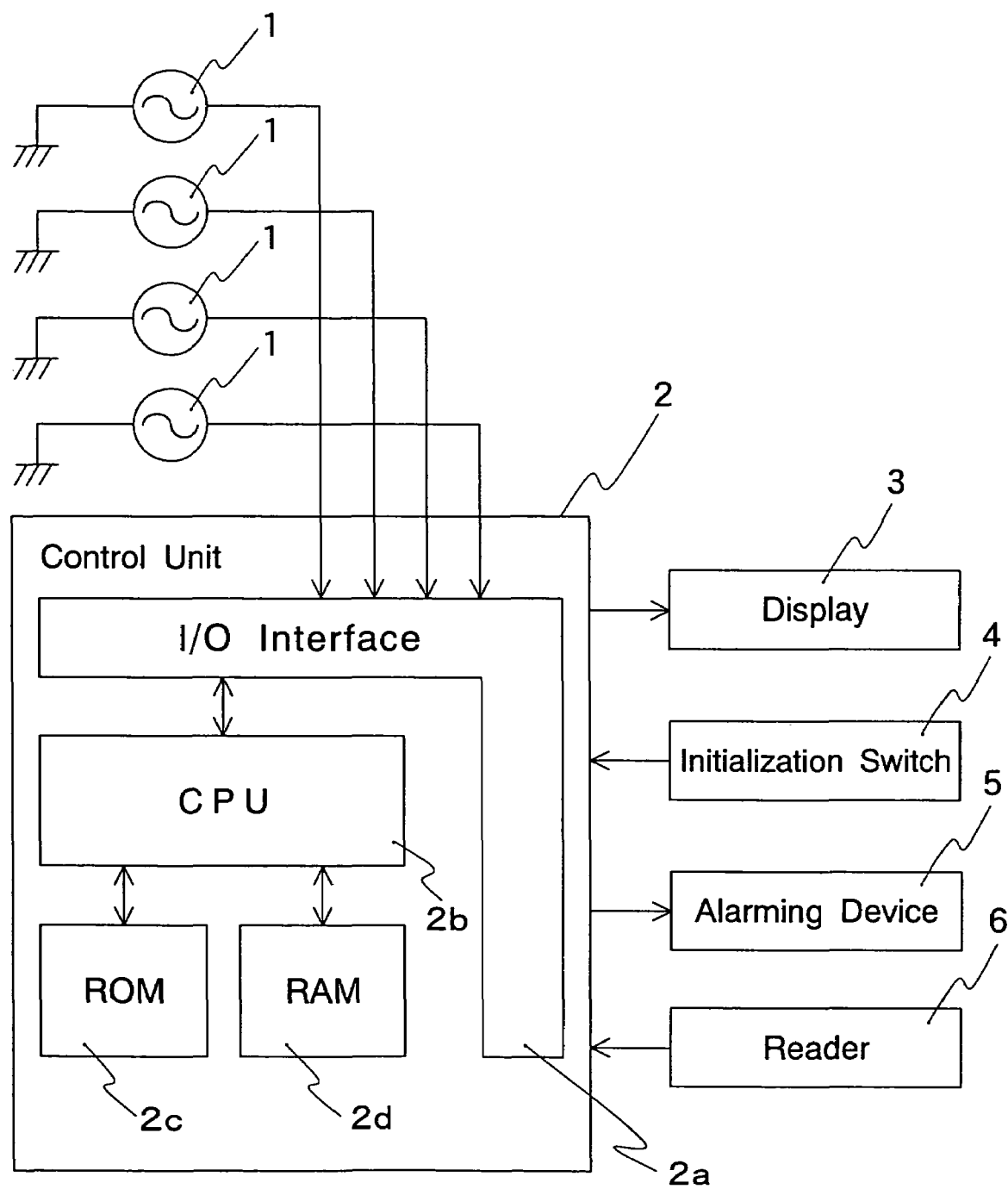
FIG. 2 is a block chart showing the electric constitution of the road surface condition-judging device of FIG. 1.

As represented in FIG. 2, the control unit 2 is composed of an I/O interface 2a which is necessary for transferring signals with external devices, a ROM 2c in which the control operation program for said CPU 2b was stored, and a RAM 2d in which data are temporarily downloaded and the downloaded data and the like are read out when the CPU 2b carries out control operation.

The rotational speed-detecting means 1 outputs pulse signals (hereinafter, referred to as wheel speed pulses) corresponding to the rotation numbers of tires. Further, CPU 2b calculates the rotational angular velocities, Fi, of the respective tires by every fixed sampling cycle, $\Delta T$ (sec), for example, by every $\Delta T=1$ second, based on the wheel speed pulses which were output from the rotational speed-detecting means 1.

By the way, since tires are produced including unevenness (initial difference) within specification, the effective rolling radii (a value obtained by dividing a distance proceeded by one rotation, by $2\pi$) of respective tires are not always the same even if all tires have normal air pressure. Accordingly, the rotational angular velocities, Fi of respective tires come to be uneven. Therefore, for example, there is a method of excluding the influence of initial difference from the rotational angular velocities, Fi. Firstly, the method calculates initial correction coefficients K1, K2 and K3 which are shown as follows:

$$K1 = F1/F2 \tag{1}$$

$$K2 = F3/F4 \tag{2}$$

$$K3 = (F1 + K1 \times F2)/(F2 + K2 \times F4) \tag{3}$$

Hereat, F1 to F4 are respectively the rotational angular velocities of a front left tire, a front right tire, a rear left tire and a rear right tire. Subsequently, new the rotational angular velocities, $F1_i$ are determined using the initial correction coefficients K1, K2 and K3 which were thus calculated, as shown in the equations (4) to (7).

$$F1_1 = F1 \tag{4}$$

$$F1_2 = K1 \times F2 \tag{5}$$

$$F1_3 = K3 \times F3 \tag{6}$$

$$F1_4 = K2 \times K3 \times F4 \tag{7}$$

Herein, the initial correction coefficient, K1 is a coefficient for correcting the difference of effective rolling radius which is caused by the initial difference between left and right front tires. The initial correction coefficient, K2 is a coefficient for correcting the difference of effective rolling radius caused by the initial difference between left and right rear tires. The initial correction coefficient, K3 is a coefficient for correcting the difference of effective rolling radius caused by the initial difference between a left front tire and a left rear tire. Then, the wheel speed of a tire of each wheel, Vi is calculated based on the $F1_i$. In the present invention, the rotational speed of a tire is a product of the rotational angular velocity of a wheel with the effective rolling radius of the tire.

In the present mode of operation, the judgment device of road surface condition is composed of the wheel speed-detecting means 1, a memory means of memorizing the rotational speed of each of tires, a slip ratio-calculating means of determining a slip ratio (a ratio of the rotational speed of front tires to the rotational speed of rear tires) from said rotational speed, an acceleration deceleration-calculating means of determining the acceleration or deceleration of the vehicle, a relation equation-calculating means of determining a relation equation between said slip ratio and the acceleration or deceleration of the vehicle, a judgment value-calculating means of determining a judgment value for judging a friction coefficient between the road surface and tires based on the slope of said relation equation determined, and a threshold-setting means of setting a threshold which is used for judging the friction coefficient from the judgment value using the information of wireless tags which were buried in the tires.

For example, the road surface, μ is judged by the threshold below (0.12 and 0.18), by setting the slope of the relation equation as a linear regression coefficient, K between a slip ratio and the acceleration or deceleration of a vehicle which is the judgment value of road surface.

$$\begin{array}{ll} K \leq 0.1 & \text{High } \mu \text{ road } (\mu = 0.7 \text{ or more}) \\ 0.1 < K \leq 0.16 & \text{Medium } \mu \text{ road } (\mu = 0.3 \text{ to } 0.7) \\ 0.16 < K & \text{Low } \mu \text{ road } (\mu = 0.3 \text{ or less}) \end{array} \tag{8}$$

The threshold of the regression coefficient, K can be obtained from the experimental data hetherto by every tire which was preliminarily set.

In the present mode of operation, the rotational speeds of tires of the four wheels are detected at 0.1 second or less, and preferably 0.05 second or less. The acceleration or deceleration of a vehicle can be determined by being measured with a G sensor, but it is preferable from the viewpoint of cost that it is calculated from the average rotational speed of the four wheels or coupled driving wheels.

Then, the moving average of the slip ratio and the acceleration or deceleration of a vehicle is determined as the average of data for a fixed time, for example, data for 0.1 second or more, by every sampling time, and the relation equation between said slip ratio and said acceleration or deceleration of a vehicle is determined based on the value of moving average (the slip ratios of a fixed number and the acceleration or deceleration of a vehicle).

Further, the mutual linear regression coefficient between a slip ratio and the acceleration or deceleration of the vehicle, and the correlative coefficient are determined using the data obtained from the moving average of the slip ratios and the acceleration or decelerations of a vehicle, for example, at least 5 or more of data. Hereat, when the slip ratio which was obtained from the moving average is a fixed value or more (for example, when it is 0.07 or more, or −0.07 or less), it is not used for the calculation of regression coefficient, it may be alarmed as slip alarm.

In the present mode of operation, when it is input that tires were exchanged, the discrimination information is obtained from the wireless ID tags. The discrimination information is a maker, a tire size, the kind of size and the like. For example, when it recognizes studless winter tires, new threshold, SS is calculated base on size information, maker information and the like.

For example, when the threshold at a basis size and basis tires (tires when standard installation is tires for summer) was S, the new threshold SS can be set based on (1) to (4) below.

(1) It is lessened by 1% by every magnification of 10 mm of the size of tire width.

(2) It is enlarged by 1% by every magnification of 10 mm of the height of tires.

(3) It is enlarged by 25% when tires are studless winter tires.

(4) It is enlarged by 12% when tires are tires for all seasons.

Further, a correction coefficient, a can be also multiplied depending on a maker or a pattern (for example, Winter Sport M3 manufactured by German Dunlop Co.). For example, it is α=1.0 in case of tires for summer, it is α=1.25 in case of the studless winter tire and α=1.12 in case of tires for all seasons.

Firstly, when the judgment value of road surface judged by the judgment value-calculating means is larger than the threshold, S, the judgment of road surface can be carried out when the friction coefficient, μ of tire at installation is lowered.

When values after change of tire width and tire height are respectively T' and H', the new threshold, SS can be represented as follow.

$$SS = S \times \{1 + (T'-T)/1000\} \times \{1 + (H'-H)/1000\} \times \alpha \tag{9}$$

Then, the judgment of road surface is carried out by the new threshold, SS in place of the equation (8).

Further, the new threshold, SS is compared with the judgment value (for example, the value of the linear regression coefficient, K) of road surface judged when a vehicle runs really on various road surfaces. Firstly, when studless winter tires (used studless winter tires) whose abrasion has proceeded are installed, the vehicle at running on snow and ice is apt to slip more easily than running at new tires, and it is dangerous. However, since it can be detected by the judgment of road surface that it is apt to slip easily, safe running can be carried out by alarming it to a driver. To the contrary, when a vehicle runs on an asphalt road, the judgment value for judging the slipperiness of road surface is lessened because the stiffness of tread becomes higher caused by abrasion, therefore the judgment value of road surface reveals a value without slipping which does not exceed the new threshold, SS.

Accordingly, when the judgment that there is no slip at which the judgment value of road surface does not exceed the new threshold, SS is frequently provided, it means that the abrasion of studless winter tires has proceeded, therefore it can be grasped that the abrasion condition of used studless winter tires (for example, 25%, 30% or 50%) can be judged by comparing the new threshold, SS with the judgment value of road surface.

Thus, the generation of false alarm can be prevented by changing the threshold being the judgment basis of the slipperiness of road surface according to the transmitting information of wireless tags.

Further, the threshold at new articles of the studless winter tires can be calculated from the information of kind of tires by the information of threshold in tires for summer and the information of wireless tags concerning the studless winter tires. The abrasion condition of the tires can be deduced by comparing the threshold at the new articles of the studless winter tires with the judgment value of road surface when a vehicle runs on asphalt.

Then, the present invention is illustrated based on Examples, but the present invention is not limited to only such Examples.

EXAMPLE 1

BMW328i mounting a reader for wireless ID tags was prepared as a vehicle. After tires having a tire size of 205/55ZR16 SP9000 (a tire width of 215 mm, an outer diameter of 631 mm and a tire height of 113 mm) were installed as the basis tires, it run on the Okayama Test Course of Sumitomo Rubber Industry Co., Ltd. (an asphalt road with a friction coefficient, μ of nearly 1.0 and a porcelain tile road with a friction coefficient, μ of nearly 0.1). The friction coefficient, μ is the maximum values for the basis tires, respectively.

Then, the following four kinds of tires, A, B, C and D were used as tires for test in which the wireless ID tags were buried.

(1) Tires A

A tire size is 215/45R17 SP9000 (tires for summer: a tire width of 220 mm, an outer diameter of 623 mm and a tire height of 96 mm).

(2) Tires B

A tire size is 205/55R16 DS2 (studless winter tires: a tire width of 205 mm, an outer diameter of 633 mm and a tire height of 113 mm).

(3) Tires C

A tire size is 205/55R16 SP Winter Sport M3 (tires for all seasons: a tire width of 215 mm, an outer diameter of 631 mm and a tire height of 113 mm).

(4) Tires D

A tire size is 245/45R17 SP9000 (tires for summer: a tire width of 250 mm, an outer diameter of 631 mm and a tire height of 112 mm).

The result of the running tests is shown in Table 1. Further, the threshold of tires A is preliminarily retained at 0.098, and the thresholds of tires B, C and D whose threshold data are not retained are respectively 0.126, 0.113 and 0.097 according to the calculation of the equation (9).

TABLE 1

| Kind of tires | Average judgment value at running on asphalt road | Average judgment value at running on porcelain road | Threshold (new threshold) |
|---|---|---|---|
| Basis tires | 0.09 | 0.18 | 0.10 |
| Tires A | 0.09 | 0.17 | 0.098 |
| Tires B | 0.11 | 0.22 | 0.126 |
| Tires C | 0.10 | 0.21 | 0.113 |
| Tires D | 0.09 | 0.17 | 0.097 |

It can be grasped from Table 1 that when the new thresholds which were calculated from the information of wireless ID tags are used with respect to the tires B, C and D, false alarm is not emitted at the running on an asphalt road but alarm is emitted at the running on a porcelain tile road therefore the condition of road surface can be accurately judged.

EXAMPLE 2

BMW328i mounting a reader for wireless ID tags was prepared as a vehicle. Then, after tires having a tire size of 205/55ZR16 SP9000 (a tire width of 215 mm, an outer diameter of 631 mm and a tire height of 113 mm) were installed as the basis tires, it run on the Okayama Test Course of Sumitomo Rubber Industry Co., Ltd. (an asphalt road with a friction coefficient, μ of nearly 1.0). The friction coefficient, μ is the maximum value (representative value) for the basis tires.

Then, new articles and studless winter tires with an abrasion of 25% and studless winter tires with an abrasion of 50% were used as tires for test in which the wireless ID tags were buried. Further, the tire size of the studless winter tires is 205/55R16 DS2 (studless winter tires: a tire width of 205 mm, an outer diameter of 633 mm and a tire height of 113 mm).

The result of the running tests is shown in Table 2. Further, the threshold according to running by the basis tires is 0.1, and the new threshold is 0.13 according to the calculation of the equation (9).

TABLE 2

| Kind of tires | Average judgment value at running on asphalt road | Threshold (new threshold) |
|---|---|---|
| Basis tires | 0.10 | 0.10 |
| New article tires | 0.13 | 0.13 |
| Tires with an abrasion of 25% | 0.11 | 0.13 |
| Tires with an abrasion of 50% | 0.10 | 0.13 |

It can be grasped from Table 2 that the more the tires are worn, the less the average judgment value is, and the proceeding degree of abrasion can be judged by comparing them with the new thresholds in accordance with tires installed which were calculated from the information of wireless ID tags. As a result, the degree of abrasion can be judged in accordance with tires installed, and it can be alarmed to a driver that the degree of abrasion has proceeded and tires are slippery.

According to the present invention, the performance and running safety of a vehicle can be improved by reading information concerning the discrimination of tires by the transmitting information of wireless tags, and changing the threshold which is the judgment basis of slipperiness of the road surface based on the information.

Further, the abrasion condition of tires can be judged by comparing the threshold with the really calculated judgment value which judges the slipperiness of road surface, and when it is judged that abrasion has proceeded, running safety can be heightened by urging a driver to exchange tires.

It is to be understood that the above-described arrangements are only illustrative of the application of the principles of the present invention. Numerous modifications and alternative arrangements may be devised by those skilled in the art without departing from the scope of the present invention, and the appended claims are intended to cover such modifications and arrangements.

What is claimed is:

1. A device for judging road surface condition comprising:
   a wheel speed-detecting means for periodically detecting wheel rotational speeds of four wheel tires of a vehicle;
   a memory means for memorizing said wheel rotational speed of each tires;
   a slip ratio-calculating means for determining a slip ratio from said wheel rotational speeds;
   an acceleration deceleration-calculating means for determining acceleration or deceleration of said vehicle;
   a relation equation-calculating means for determining a relation equation between said slip ratio and said acceleration of said vehicle;
   a judgment value-calculating means for determining a judgment value for judging a friction coefficient between road surface and tires based on slope of said relation equation determined; and
   a threshold-setting means for setting a threshold used for judging friction coefficient from said judgment value with information of wireless tags buried in said tires.

2. The device for judging road surface condition of claim 1, wherein, the information provided by the wireless tags includes (1) the maker of the tires, (2) the size of the tires and (3) the service type of the tires.

3. A program, provided in machine-readable memory of a control unit, for judging road surface condition, the program, when executed, causing the control unit to function as:
   a memory means for memorizing wheel rotational speed of each tires mounted on a vehicle;
   a slip ratio-calculating means for determining a slip ratio from said wheel rotational speeds;
   an acceleration deceleration-calculating means for determining acceleration or deceleration of said vehicle;
   a relation equation-calculating means for determining a relation equation between said slip ratio and said acceleration of the vehicle;
   a judgment value-calculating means for determining a judgment value for judging a friction coefficient between road surface and said tires based on slope of said relation equation determined; and
   a threshold-setting means for setting a threshold used for judging friction coefficient from said judgment value with information of wireless tags buried in said tires.

4. The device for judging road surface condition of claim 1 further comprising an abrasion-judging means for judging the abrasion condition of tires by said threshold set.

5. The program for judging road surface condition of claim 3, wherein, the information provided by the wireless tags includes (1) the maker of the tires, (2) the size of the tires and (3) the service type of the tires.

6. The program for judging road surface condition of claim 3, wherein the control unit is further caused to function as an abrasion-judging means for judging abrasion condition of tires by said threshold set.

* * * * *